United States Patent [19]
Lucey, Jr. et al.

[11] Patent Number: 6,044,293
[45] Date of Patent: Mar. 28, 2000

[54] METHOD FOR DETECTING TOXIC CHEMICAL CONCENTRATION IN INDIVIDUALS

[75] Inventors: George K. Lucey, Jr., Burtonsville; Melvyn J. Shichtman, Reisterstown, both of Md.

[73] Assignee: Altec, Inc., Boston, Mass.

[21] Appl. No.: 09/197,757

[22] Filed: Nov. 23, 1998

[51] Int. Cl.[7] .................................................. A61B 5/00
[52] U.S. Cl. .............................................................. 600/546
[58] Field of Search .................................... 600/544, 545, 600/546, 547, 591

[56] References Cited

U.S. PATENT DOCUMENTS

| | | | |
|---|---|---|---|
| 4,715,386 | 12/1987 | Martin | 600/546 |
| 5,092,343 | 3/1992 | Spitzer et al. | . |
| 5,163,440 | 11/1992 | DeLuca et al. | . |
| 5,195,531 | 3/1993 | Bennett | 600/546 |
| 5,368,042 | 11/1994 | O'Neal et al. | . |
| 5,957,860 | 9/1999 | Olive | 600/546 |

*Primary Examiner*—Max Hindenburg
*Attorney, Agent, or Firm*—John E. Toupal; Harold G. Jarcho

[57] ABSTRACT

A method for detecting in a human test subject the presence of a harmful level of a chemical-biological agent, the method including the steps of administering a given dose of a predetermined chemical-biological agent to a control subject; extracting control EMG signals from the control subject; processing the control EMG signals to determine given parameters thereof; and storing data obtained in the processing step. The above steps are repeated for a plurality of other control subjects and the resultant data are used to determine the given dose of the predetermined chemical-biological agent a standard range of the given parameters. All of the above steps are repeated with each of a plurality of different sized chemical-biological doses of the predetermined chemical-biological agent and all resultant data are used to determine a normative range of the given parameters for each of the plurality of different sized chemical-biological doses. After establishing the normative ranges, EMG test signals are extracted from the human test subject and processed to determine the given parameters which then are compared to the data normative to determine the concentration in the test subject of the predetermined chemical-biological agent.

22 Claims, 11 Drawing Sheets

FIG. 11

METHOD FOR DETECTING TOXIC CHEMICAL CONCENTRATION IN INDIVIDUALS

BACKGROUND OF THE INVENTION

The invention relates generally to a method for detecting toxic chemical concentration in an individual and, more particularly, to such a method employing electromyographic (EMG) signals as a detection mechanism.

There are a number of agents used for chemical warfare including Nerve Agents, Toxins, Blister Agents, Blood Agents, and Incapacitating Agents. Of these the most threatening are the Nerve Agents [Soman (GD), Sarin (GB), Four-Amino Pyridine (4-AP), Tabun (GA), and VX] and the Neuro Toxins [Saxitoxin (STX) and Tetrodotoxin (TTX)]. The world-wide military community addresses these threats with environmental alarms, protective clothing, and medical responses. The sensitivity of field alarms and the life-cycle of protective clothing are limited, however, so individual exposures are to be expected. Similarly, exposures in the civilian population may be expected in the agriculture, insecticide, manufacturing, fire fighting, hazmat transportation, and police communities.

The effects of exposure will depend upon the type of chemical, concentration, length of exposure, and method of exposure (skin, wound, mouth, lung, eye). If high concentrations appear in the blood stream, the effect may be lethal and a medical response within minutes may be required. If low concentrations appear in the blood stream, then natural recovery without medical attention may be possible.

Low level exposures cannot be ignored since the effects are cumulative and multiple exposures may result in a casualty. Immediate evacuation after the first exposure is crucial, but the problem is to identify individuals who have been exposed if the concentrations are too low to be detected by existing field alarms. Two methods currently employed are blood tests and observation of physiological symptoms. Blood testing such as for reduced levels of actylcholinesterase is accurate but impractical due to the length of time required for analysis and due to the large numbers of false alarms that will also draw blood. As a result, reliance world-wide is based upon subjective visual observations.

The physiological symptoms of exposure vary with the chemical agent and concentration. These can include: headache, slurred speech, fatigue, nausea, hallucination, runny nose, impaired night vision, degraded short range vision, pinpointing of the eyes, tightness of the chest, excessive sweating and salivating, excessive urination and defecation, muscle spasms, weakness, convulsion, respiratory and cardiac failure. For low-level exposures the effects are reduced and the symptoms may be ignored or go unrecognized.

The object of this invention, therefore, is to provide an improved method for detecting the presence of toxic biological-chemicals in individuals having been exposed to such agents.

SUMMARY OF THE INVENTION

The invention is a method for detecting in a human test subject the presence of a harmful level of a chemical-biological agent, the method including the steps of administering a given dose of a predetermined chemical-biological agent to a control subject; extracting control EMG signals from the control subject; processing the control EMG signals to determine given parameters thereof; and storing data obtained in the processing step. The above steps are repeated for a plurality of other control subjects and the resultant data is used to determine for the given dose of the predetermined chemical-biological agent a standard range of the given parameters. All of the above steps are repeated with each of a plurality of different sized chemical-biological doses of the predetermined chemical-biological agent and all resultant data is used to determine a normative range of the given parameters for each of the plurality of different sized chemical-biological doses. After establishing the normative ranges, EMG test signals are extracted from the human test subject and processed to determine the given parameters which then are compared to the normative data to determine the concentration in the test subject of the predetermined chemical-biological agent. Finally, decisions are made regarding an appropriate medical response.

According to features of the invention, the given parameters are time dependent and include, for example, voltage, power, and frequency characteristics of the EMG signals. These parameters provide particularly useful data.

According to other features of the invention, the chemical-biological chemical is a Nerve Agent or a Neuro Toxin. These agents can require specific and rapid medical treatment.

Another embodiment of the invention includes the steps of sequentially administering a given dose of each of a plurality of different predetermined chemical-biological agents to a control subject; extracting after each administering step EMG signals from the control subject; processing the control EMG signals to determine given parameters thereof associated with each predetermined agent; and storing data obtained in the processing steps. The above steps are repeated for a plurality of other control subjects and the resultant data is utilized to determine for the given dose of each predetermined chemical-biological agent a standard range of the given parameters. All of the above steps are repeated with each of a plurality of different sized chemical-biological doses of each predetermined chemical-biological agent and all resultant data are used to determine a normative range of the given parameters for each of the different sized doses of each chemical-biological agent. After establishing the normative ranges, EMG test signals are extracted from the human test subject and processed to determine the given parameters which are compared to the normative data to determine the concentrations in the test subject of each predetermined chemical-biological agent. Finally, decisions are made regarding an appropriate medical response.

According to specific features of the above embodiment, the method includes the further steps of providing a detector assembly for extracting EMG signals; the detector assembly having a flexible substrate with an adhesive surface, spaced apart electrodes for extracting EMG signals, a power supply, a differential amplifier for receiving signals from the electrodes, a signal processor for processing EMG signals, and a storage system for storing data provided by the processing system. The adhesive surface of the detector assembly is secured to the skin of the human test subject and used to provide the above described test signals.

According to other features of the above embodiment, the detector assembly further includes telemetry and the method includes the step of transmitting data from the detector assembly to a processing unit at a remote location for processing. These features facilitate agent testing of subjects in remote areas of activity, and a personal alarm system for indicating exposure.

According to additional features, the above embodiment includes the steps of removing the detector assembly from the test subject; downloading data from the storage system to a processing unit; and processing data with the processing unit. These features allow miniaturization of the detector assembly.

According to yet other features, the above embodiment includes the steps of recharging the power supply; and securing the adhesive surface of the detector assembly to the skin of another human test subject. These steps enhance economic viability of the method.

DESCRIPTION OF THE DRAWINGS

These and other objects and features of the invention will become more apparent upon a perusal of the following description taken in conjunction with the accompanying drawings wherein:

FIG. 11 depicts expected median frequency-time curves for EMG signals from guinea pigs injected with three different dose concentrations of STX.

DESCRIPTION OF PREFERRED EMBODIMENTS

Figure 1:
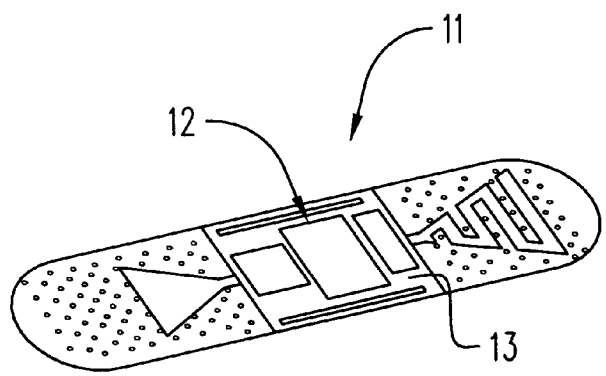
FIG. 1 is a top view of a detector assembly according to the invention.
Figure 1A:
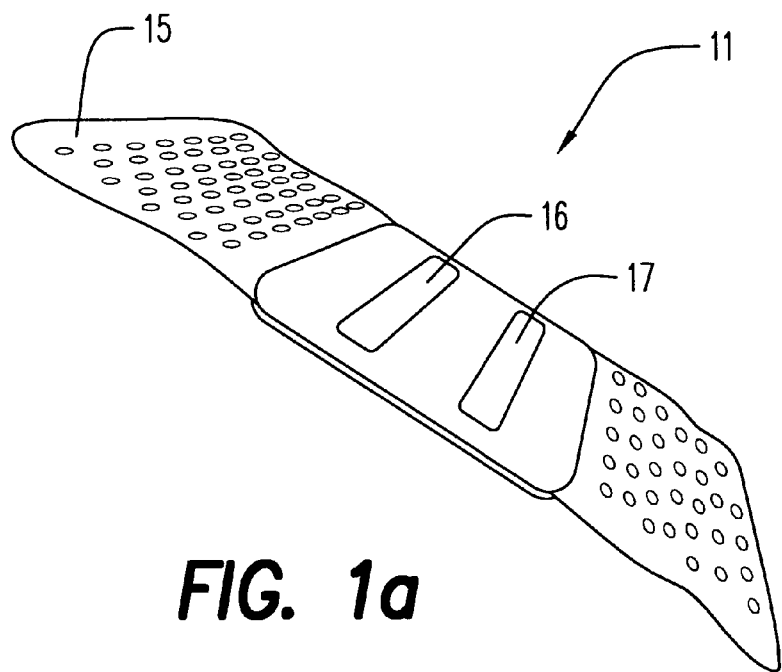
FIG. 1a is a bottom view of the detector assembly shown in FIG. 1.
Figure 2:
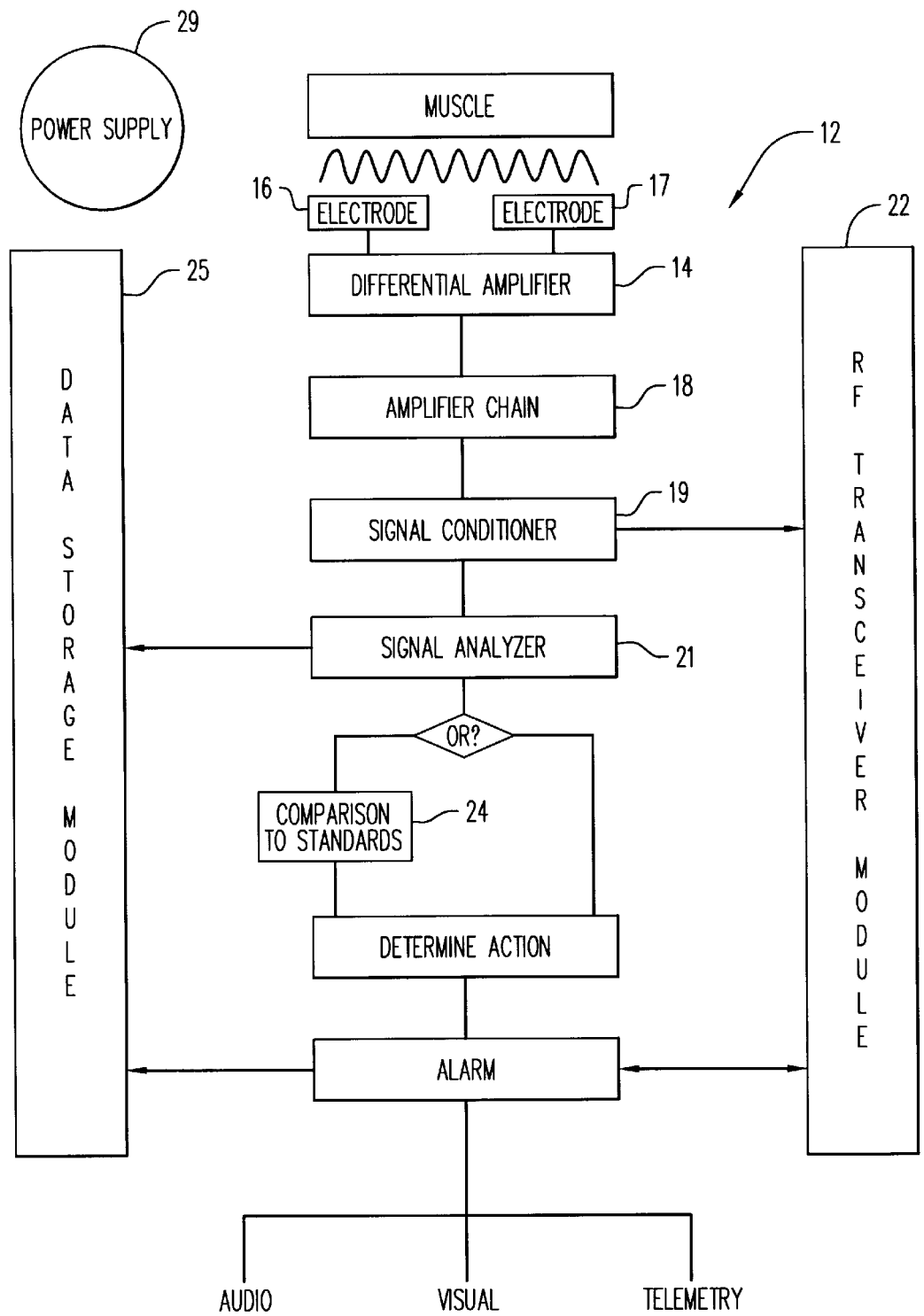
FIG. 2 is a block circuit diagram of an electronic circuit of the detector assembly shown in FIG. 1.

Detection of chemical-biological agents is implemented with a detector assembly 11 for extracting, conditioning and analyzing EMG signals. The detector assembly 11 includes electronic circuitry 12 (FIG. 2) mounted on a BandAid type substrate 13 (FIGS. 1 and 1a) having an adhesive bottom surface 15. Included in the circuitry 12 is a differential amplifier 14 that receives EMG signals from a pair of elongated, parallel electrodes 16, 17 and transmits amplified signals to an amplifier chain 18 and a signal conditioner 19. After being conditioned in the conditioner 19, the signals are fed into a signal analyzer 21 and an RF transceiver module 22. The signals received from the analyzer 21 are compared in a comparison module 24 to standard signal data retained in a data storage module 25 which also retains data provided by the comparison module 24. Alternatively, the signals from the analyzer 21 are used directly to determine the course of action. In the event that the comparison made in the module 24 indicates an excessive concentration of harmful chemical agents, an alarm 28 is activated to provide either a visual or audible indication. The alarm 28 also communicates with the transceiver module 22 and the storage module 25. Power is provided by a battery power supply 29. Preferably, the substrate 13 and the circuitry 12 are designed to render the detector assembly 11 soft, flexible, bendable and twistable so as to alleviate signal deterioration and user discomfort when mounted on the skin of a human test subject. Specific details of the circuitry 12 are known and disclosed, for example, in U.S. Pat. Nos. 5,092,343; 5,163,440 and 5,368,042.

Figure 3:
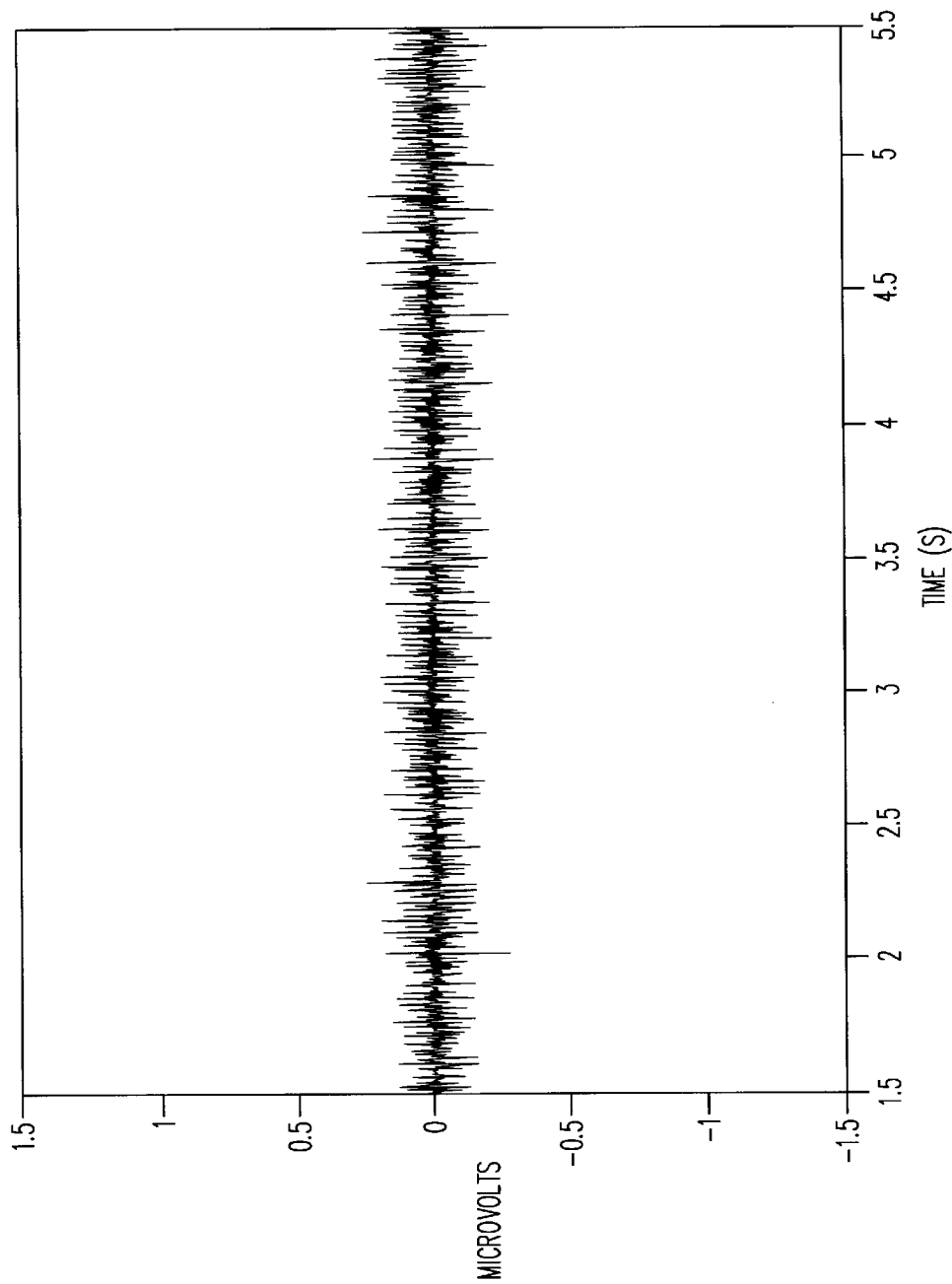
FIG. 3 is a voltage-time signature of an EMG signal measured at the neck muscle of a guinea pig before an injection of STX.
Figure 4:
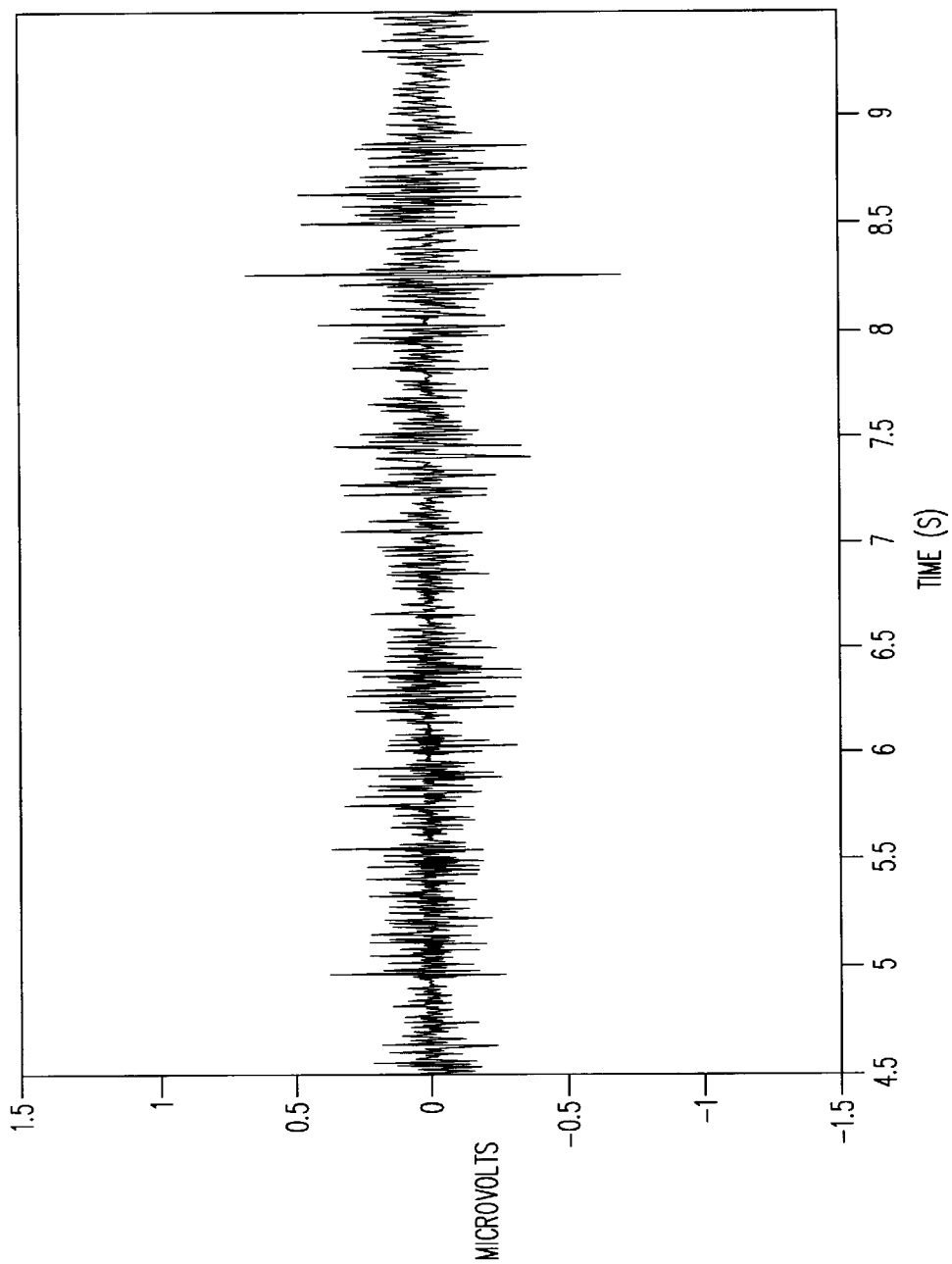
FIG. 4 is a voltage-time signature of an EMG signal measured at the neck muscle of the guinea pig used for FIG. 3 after an injection of a lethal dose of STX.

The detector assembly 11 can be used to detect, in a human test subject, exposure levels to Nerve Agents and Neuro Toxins which can detrimentally affect the nervous system. In the instance of Nerve Agents, actylcholinesterase is deactivated in the nerve and muscle synapses and excess acetylcholine over stimulates the nervous system. In the instance of Neuro Toxins, either the acetylcholine receptors are blocked in the synapses and or the flow of ions through the nerve membrane is diminished. Both mechanisms distort the EMG signal signature. Such distortion is evidenced in FIGS. 3 and 4 which illustrate, respectively, voltage vs. time for EMG signals obtained with needle electrodes embedded in the neck muscles of a guinea pig immediately before and for about ten minutes after a lethal injection of Saxitoxin (STX).

Dangerous levels of a given chemical agent in a test subject are detected in accordance with the invention by comparing EMG signals obtained from the test subject with critical parameter standards obtained by analyzing EMG signal changes that occur after injections of specific chemicals into animals such as guinea pigs and Rhesus monkeys. To isolate the critical parameters that may be used in an alarm system to provide reliable early warning of chemical exposure, the analog data obtained from test animals is digitized, subjected to conventional analyses of curve shapes, peaks, areas, frequencies, power, etc., and then examined for measurable changes after the chemical exposure. Such standards require a generation of data base EMG signatures obtained by testing statistically significant quantities of animals subjected to different chemicals at different concentrations.

Figure 5:
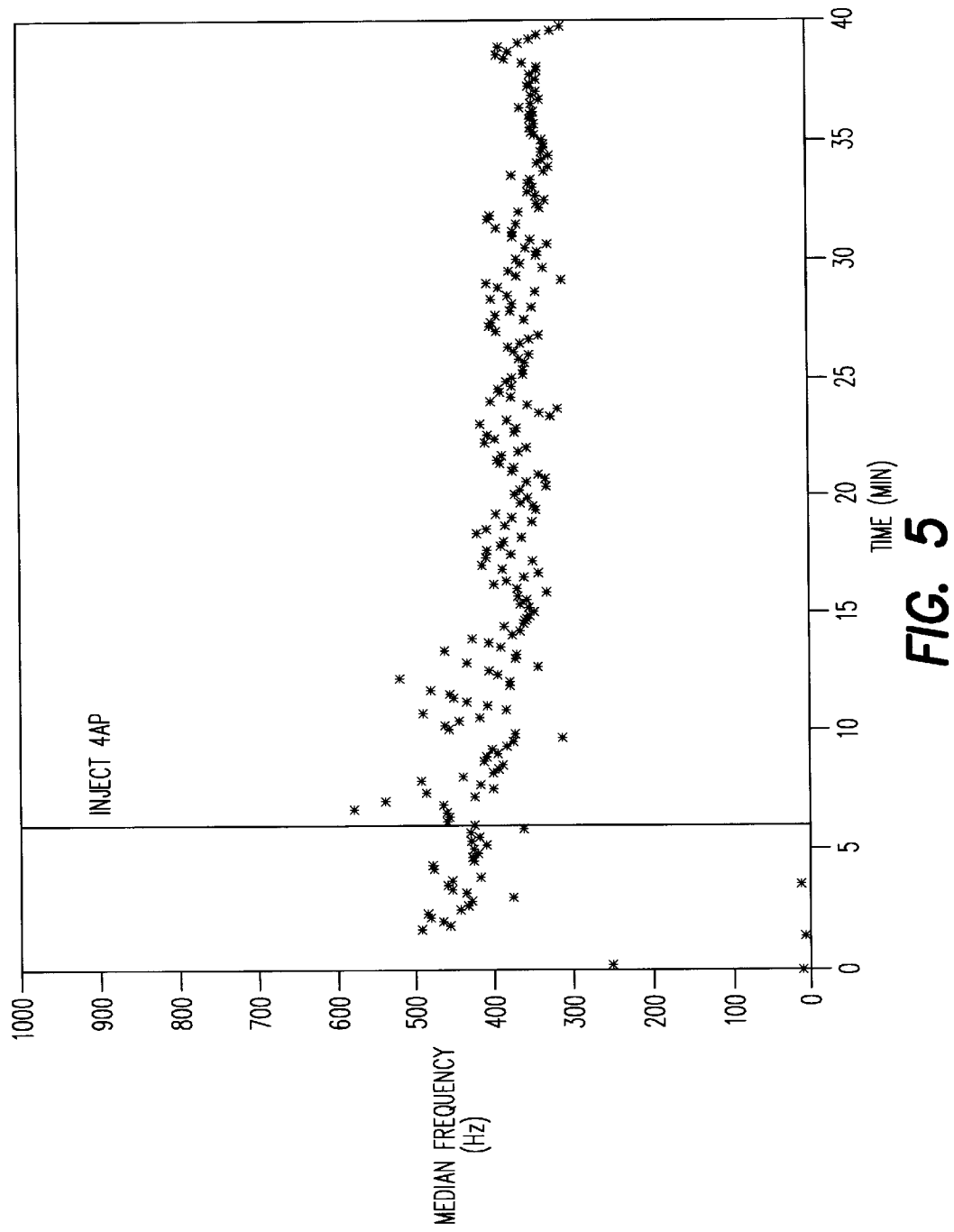
FIG. 5 is a median frequency-time plot of an EMG signal measured at the neck muscle of a guinea pig after injection of a non-lethal dose of 4AP.
Figure 6:
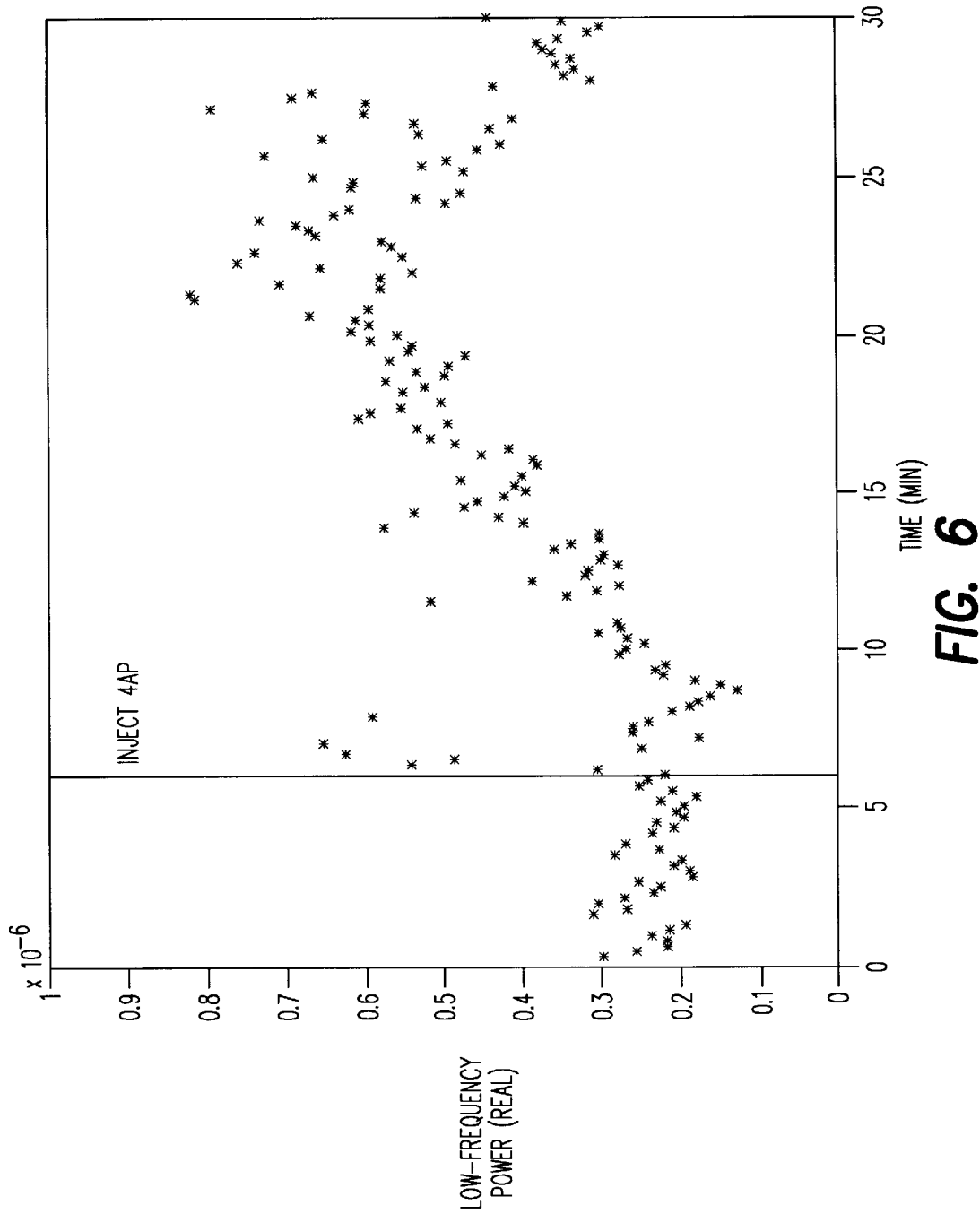
FIG. 6 is a low frequency-time plot of the EMG signal used for FIG. 5.
Figure 7:
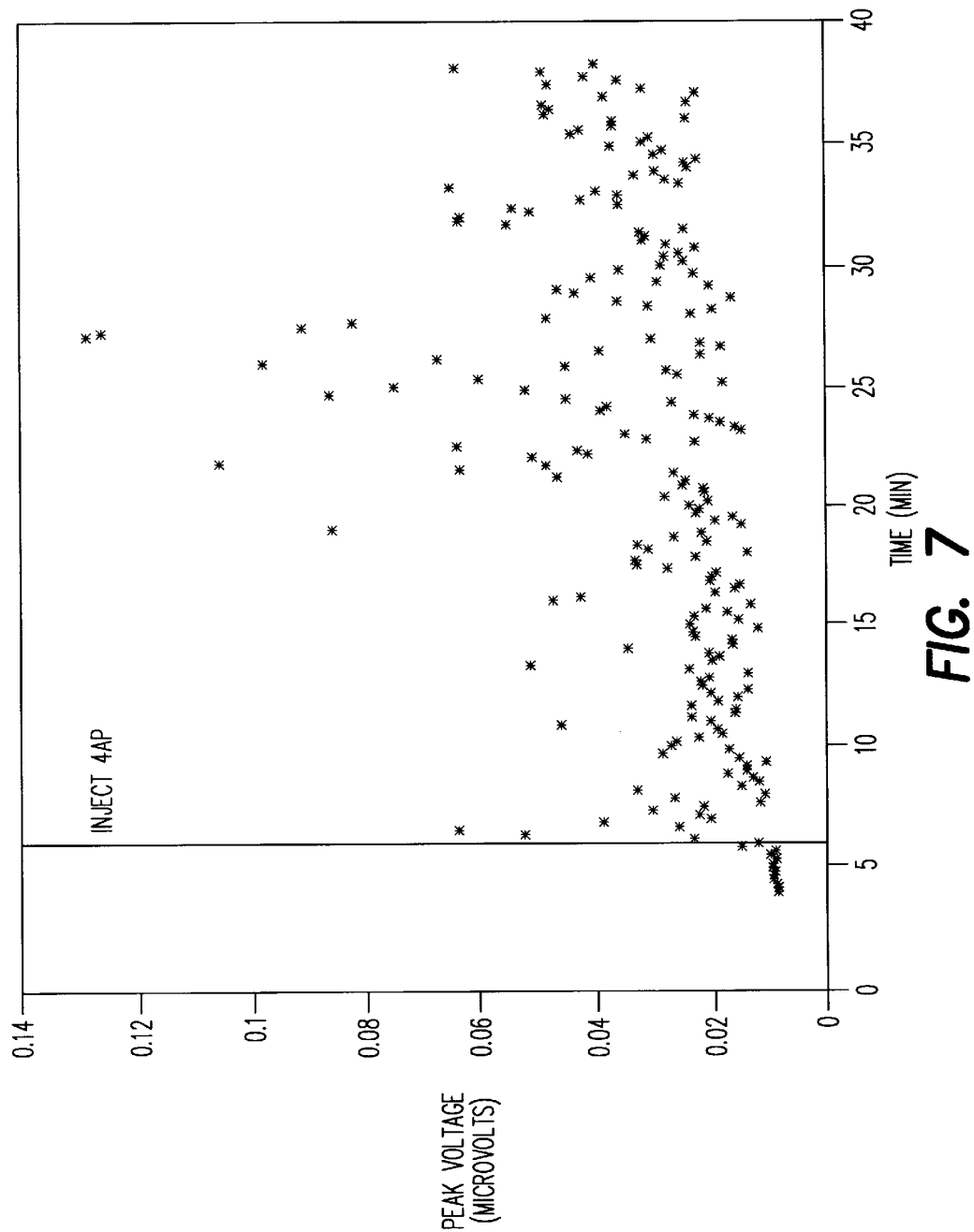
FIG. 7 is a peak voltage-time plot of the EMG signal used for FIG. 5.

FIGS. 5–7 illustrate three critical parameters derived by injecting a guinea pig with a non-lethal dose of a sodium channel blocker Four-Amino Pyridine (4-AP). As shown in FIG. 5, median frequency of the resultant EMG signal decreases with time almost instantaneously after the injection. Conversely, low-frequency power and peak voltage increase with time as shown, respectively, in FIGS. 6 and 7.

Figure 8:
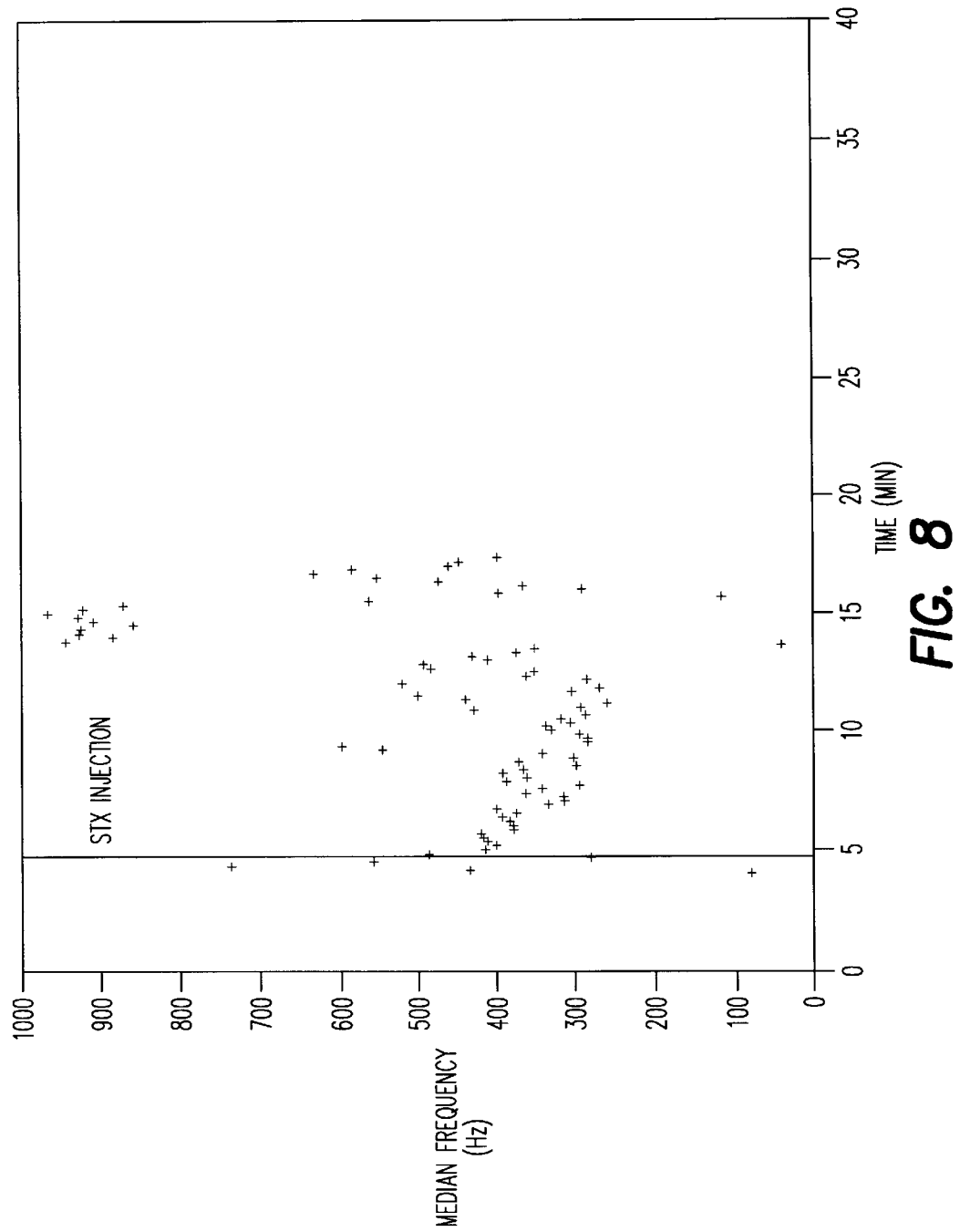
FIG. 8 is a median frequency-time plot for an EMG signal measured at the neck muscle of a guinea pig after injection of a lethal dose of STX.
Figure 9:
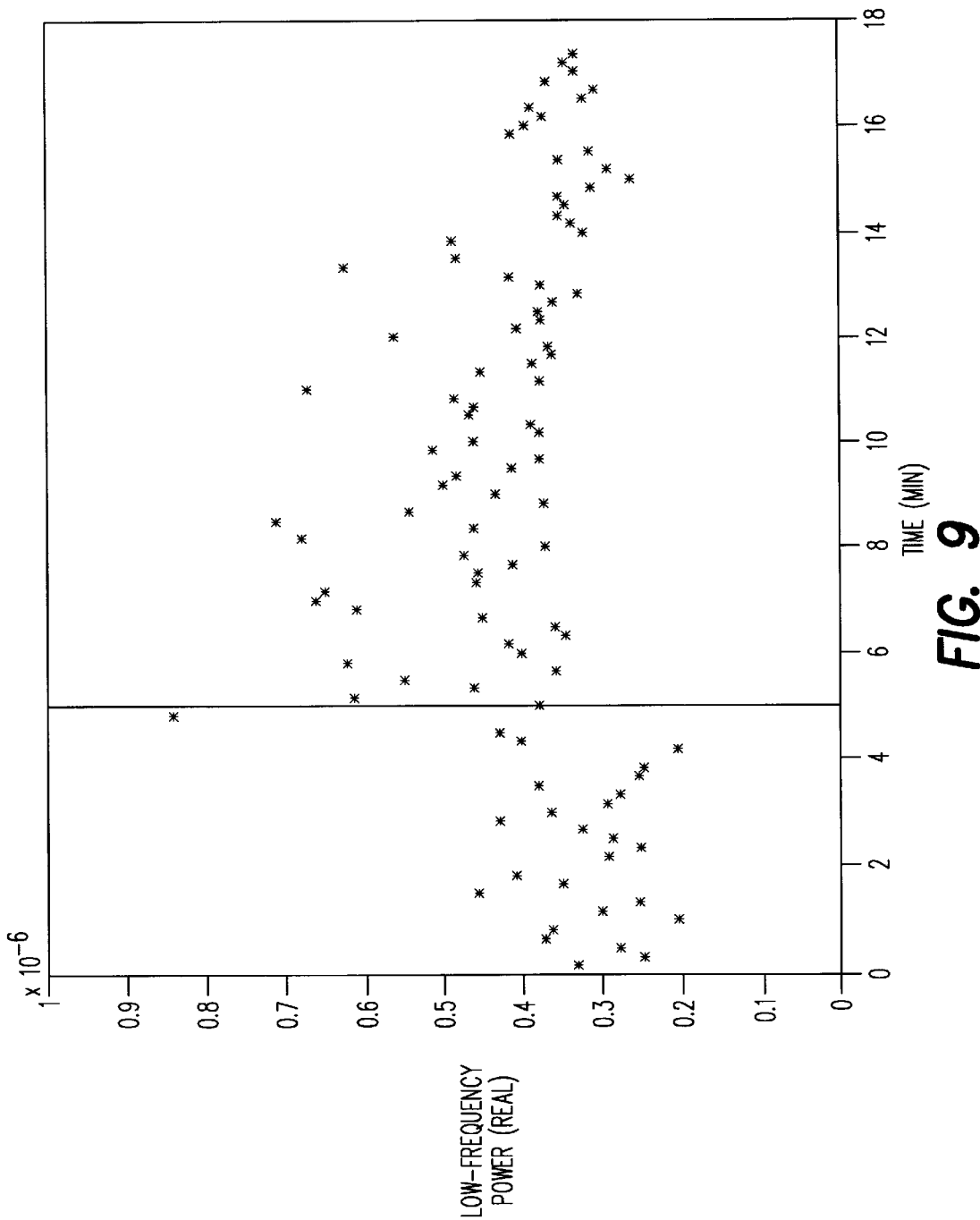
FIG. 9 is a low frequency-time plot of the EMG signal used for FIG. 8.
Figure 10:
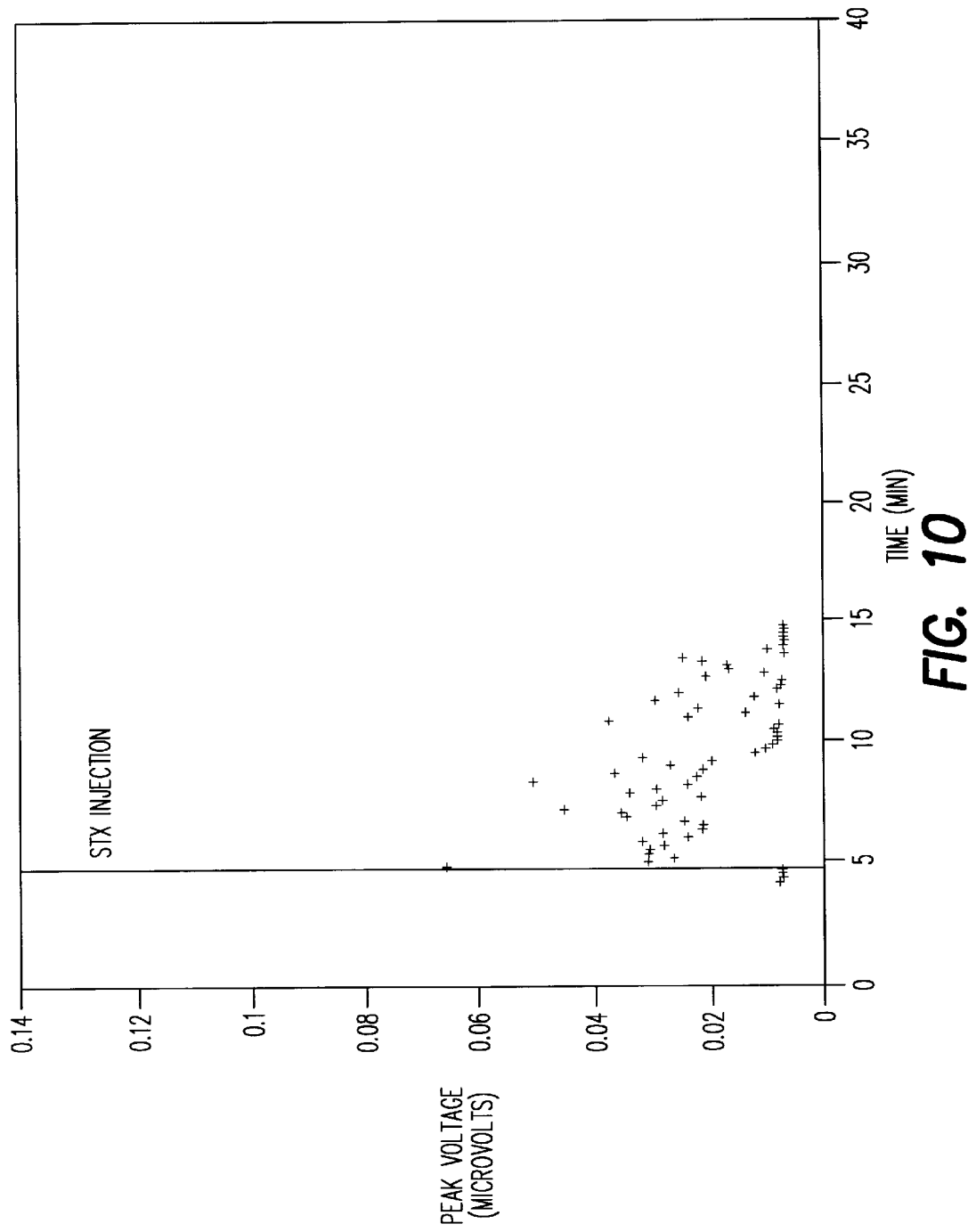
FIG. 10 is a peak voltage-time plot of the EMG signal used for FIG. 8.

FIGS. 8–10 illustrate three different critical parameters derived by injecting a guinea pig with a lethal dose of a potassium channel blocker Saxitoxin (STX). As shown in FIG. 8 median frequency of the resultant EMG signal increases rather than decreases with time while Peak Power exhibits little change as shown in FIG. 9. Also, peak voltage decreases rather than increases with time as shown in FIG. 10. Thus, different types of channel blockers produce different, distinguishable critical parameter standards.

Figure 11:
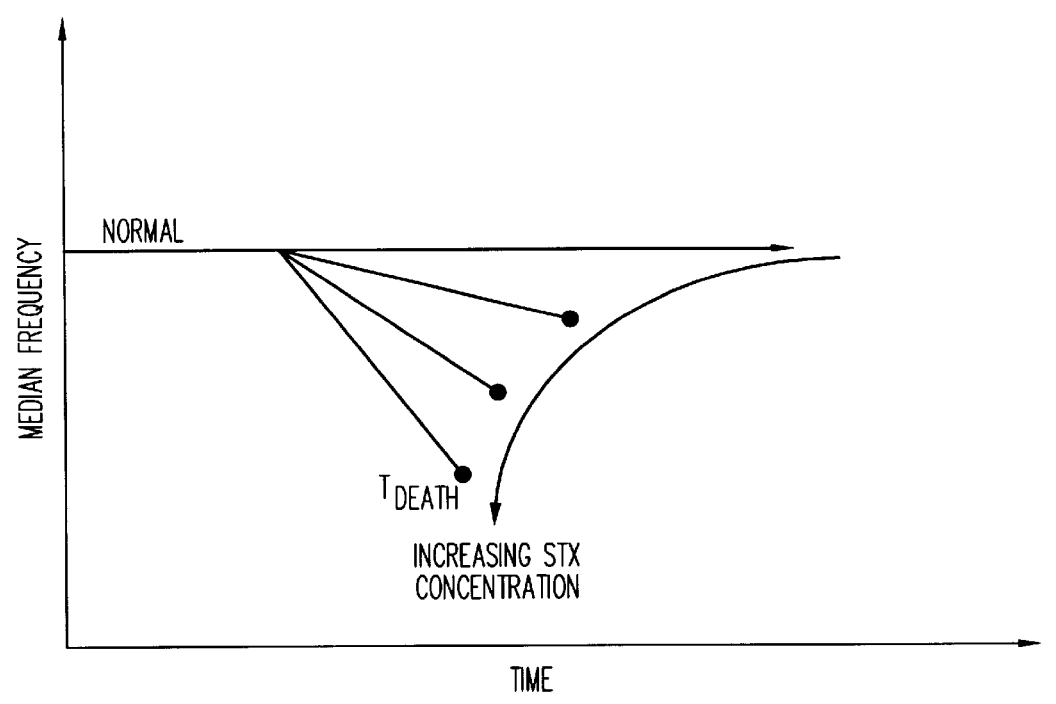

FIG. 11 shows an expected effect of 4-AP concentration on the slope of median EMG frequency and on life span. The trends indicated were determined by experience rather than actual data. As shown, low level concentrations do not result in death and consequently have no finite duration. Higher concentrations, however; are shown with steeper slopes to reflect faster degradation of the nervous system and shorter duration to reflect reduced life expectancy. Similar trend analyses can be established for other critical parameters.

In use, the detector assembly 11 is affixed to individuals operating at risk of exposure to biological-chemicals. Specific usage would entail monitoring exposure of troops in a chemically contaminated battlefield. Other individuals at risk by exposure to Neuro Toxins include agricultural workers using phosphate based fertilizers, workers in chemical factories, fire fighters, police officers, security officers and others in similar occupations. The detector assembly 11 is adhered to the skin above a muscle, such as the neck muscle, to be monitored. One or more detector assemblies can be affixed depending upon the information to be detected and the reliability desired.

Once attached to an individual subject, the detector assembly 11 will measure surface EMG voltages, process the signals to identify critical parameters, and compare these to known standards derived as described above. In the event that one or more critical standards are matched, the detector assembly 11 will initiate an alarm. In addition to providing early indication of chemical exposure, the comparisons may be used to distinguish one chemical from another, calculate the time available for effective medical treatment, and assess the progress of an antidote or stimulant once applied. For some applications, raw EMG data may be telemetered in real-time to a remote data processing station for the purpose of analyzing a larger number of variables. However, if telemetry is impractical, raw EMG data may be stored in the detector assembly memory and downloaded off-line to a personal computer by means of a docking station (not shown).

Obviously, many modifications and variations of the present invention are possible in light of the above teachings. It is to be understood, therefore, that the invention can be practiced otherwise than as specifically described.

What is claimed is:

1. A method for detecting in a human test subject the presence of a harmful level of a chemical-biological agent, the method comprising the steps of:
   (a) administering a given dose of a predetermined chemical-biological agent to a control subject;
   (b) extracting control EMG signals from said control subject;
   (c) processing said control EMG signals to determine given parameters thereof;
   (d) storing data obtained in said processing step;
   (e) repeating steps (a)–(d) for a plurality of other control subjects;
   (f) utilizing said data stored in steps (d) to determine for said given dose of said predetermined chemical-biological agent a standard range of said given parameters;
   (g) repeating steps (a)–(e) with each of a plurality of different sized chemical-biological doses of said predetermined chemical-biological agent;
   (h) utilizing the data obtained in steps (g) to determine a normative range of said given parameters for each of said plurality of different sized chemical-biological doses;
   (i) extracting test EMG signals from the human test subject;
   (j) processing said test EMG signals to determine said given parameters thereof; and
   (k) comparing the data obtained in step (j) to the data obtained in steps (f) and (h) to determine the concentration in said test subject of said predetermined chemical-biological agent.

2. A method according to claim 1 wherein said given parameters are time dependent.

3. A method according to claim 1 wherein said given parameters comprise voltage characteristics of said EMG signals.

4. A method according to claim 1 wherein said given parameters comprise power characteristics of said EMG signals.

5. A method according to claim 1 wherein said given parameters comprise frequency characteristics of said EMG signals.

6. A method according to claim 1 wherein said given parameters comprise median frequency of said EMG signals.

7. A method according to claim 1 wherein said given parameters comprise voltage, power, and frequency characteristics of said EMG signals.

8. A method according to claim 1 wherein the chemical-biological chemical is a Nerve Agent or a Neuro Toxin.

9. A method according to claim 1 including the steps of responding to a given concentration of said pre-determined agent as determined in step (k) by administering a stimulant to said human test subject, and continuing to extract and process EMG signals from said test subject.

10. A method for detecting in a human test subject the presence of harmful levels of chemical-biological agents, the method comprising the steps of:
    (a) sequentially administering a given dose of each of a plurality of different predetermined chemical-biological agents to a control subject;
    (b) extracting after each administering step EMG signals from said control subject;
    (c) processing said control EMG signals to determine given parameters thereof associated with each said predetermined agent;
    (d) storing data obtained in said processing steps;
    (e) repeating steps (a)–(d) for a plurality of other control subjects;
    (f) utilizing said data stored in steps (d) to determine for said given dose of each said predetermined chemical-biological agent a standard range of said given parameters;
    (g) repeating steps (a)–(f) with each of a plurality of different sized chemical-biological doses of each said predetermined chemical-biological agent;
    (h) utilizing the data obtained in step (g) to determine a normative range of said given parameters for each of said plurality of different sized doses of each said chemical-biological agent;
    (i) extracting test EMG signals from the human test subject;
    (j) processing said test EMG signals to determine said given parameters thereof; and
    (k) comparing the data obtained in step (j) to the data obtained in steps (f) and (h) to determine the concentrations in said test subject of each said predetermined chemical-biological agent.

11. A method according to claim 10 wherein said given parameters are time dependent.

12. A method according to claim 10 wherein said given parameters comprise voltage characteristics of said EMG signals.

13. A method according to claim 10 wherein said given parameters comprise power characteristics of said EMG signals.

14. A method according to claim 10 wherein said given parameters comprise frequency of said EMG signals.

15. A method according to claim 10 wherein said given parameters comprise median frequency of said EMG signals.

16. A method according to claim 10 wherein said given parameters comprise voltage, power, and frequency characteristics of said EMG signals.

17. A method according to claim 10 wherein the chemical-biological chemical is a Nerve Agent.

18. A method according to claim 10 including the steps of responding to a given concentration of any said predetermined agent as determined in step (k) by administering a stimulant to said human test subject, and continuing to extract and process EMG signals from said test subject.

19. A method according to claim 10 wherein said step (i) comprises the steps of:

providing a detector assembly for extracting EMG signals; said detector assembly comprising a flexible substrate having an adhesive surface and retaining spaced apart electrodes for extracting EMG signals, a power supply, a differential amplifier for receiving signals from said electrodes, a signal processing means for processing EMG signals, and storage means for storing data provided by said processing means; and securing said adhesive surface of said detector assembly to the skin of the human test subject.

20. A method according to claim 19 wherein said detector assembly further comprises telemetry and including the step of transmitting data from said detector assembly to a processing unit at a remote location for performance of step (k).

21. A method according to claim 19 including the steps of:

removing said detector assembly from the test subject;

downloading data from said storage means to a processing unit; and performing step (k) with said processing unit.

22. A method according to claim 21 including the steps of:

recharging said power supply; and securing the adhesive surface of said detector assembly to the skin of another human test subject.

\* \* \* \* \*